United States Patent [19]

Krug et al.

[11] Patent Number: 5,080,794
[45] Date of Patent: Jan. 14, 1992

[54] SEPARATION OF 1-METHOXY-2-PROPANOL AND WATER

[75] Inventors: Joseph Krug, Ludwigshafen; Gernot Reissenweber, Boehl-Iggelheim; Knut Koob, Mutterstadt, all of Fed. Rep. of Germany

[73] Assignee: BASF Aktiengesellschaft, Ludwigshafen, Fed. Rep. of Germany

[21] Appl. No.: 599,835

[22] Filed: Oct. 19, 1990

[51] Int. Cl.$^5$ .............................................. B01D 61/00
[52] U.S. Cl. ................................... 210/640; 210/649; 210/651
[58] Field of Search ............... 210/640, 650, 651, 649, 210/644, 638, 653; 203/63, 64, 83

[56] References Cited

U.S. PATENT DOCUMENTS 2,981,680  4/1961  Binning ............................... 210/640

FOREIGN PATENT DOCUMENTS 1111419  4/1989  Japan ................................... 210/640

Primary Examiner—Robert A. Dawson
Assistant Examiner—Ana Fortuna
Attorney, Agent, or Firm—Keil & Weinkauf

[57] ABSTRACT

A batchwise or continuous process for separating water from a mixture of water and 1-methoxy-2-propanol by passing a heated mixture in liquid or gaseous form over a hydrophilic membrane which is selective to the passage of water.

3 Claims, 2 Drawing Sheets

SEPARATION OF 1-METHOXY-2-PROPANOL AND WATER

BACKGROUND OF THE INVENTION (1) Field of the Invention

The present invention relates to a process for separating 1-methoxy-2-propanol and water.

(2) Description of Related Art

1-Methoxy-2-propanol is frequently used as a solvent in the chemical industry, for example for chemical reactions or for recrystallizing certain compounds. After use, the 1-methoxy-2-propanol frequently contains water.

Since the mixture, by using for example simple distillation/rectification, can only be separated to the azeotrope stage and the customary methods for separating azeotropes, for example changing the pressure, azeotropic distillation, etc., are not successful, the isolation of 1-methoxy-2-propanol is inevitably very wasteful. Hitherto the azeotrope itself had to be disposed of expensively, for example by incineration.

SUMMARY OF THE INVENTION

It is an object of the present invention to avoid losses of 1-methoxy-2-propanol.

We have found that this object is achieved according to the present invention by pervaporation, a process in which the mixture is passed in liquid or gaseous form over a hydrophilic membrane.

DESCRIPTION OF THE PREFERRED EMBODIMENT

The process can be carried out industrially not only batchwise but also continuously. Both possibilities are described in detail in the following:

EXAMPLE 1

Batchwise dewatering of 1-methoxy-2-propanol by pervaporation

Figure 1:
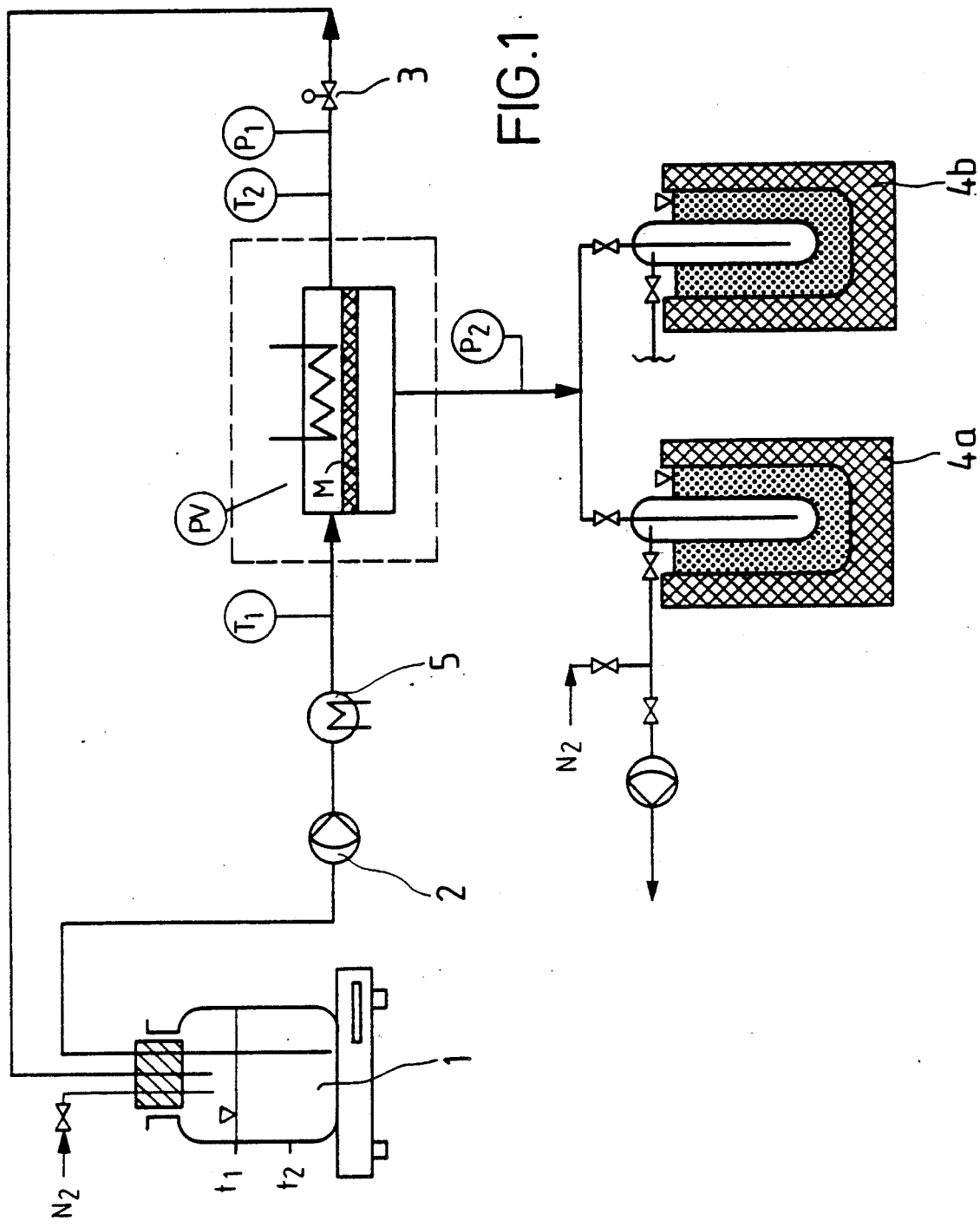
FIG. 1 shows a schematic depiction of a batchwise process according to the present invention.

The batchwise process is depicted in FIG. 1. It involves charging vessel 1 at room temperature with 718 g of a mixture of 55% by weight of 1-methoxy-2-propanol and 45% by weight of water. This charge is recycled about 7 times per hour through pump 2 and test cell PV containing 100 cm$^2$ of membrane area M. A pressure of 2.5 bar is set at the pressure control valve 3. The permeate side is under an absolute pressure of 25 mbar. The permeate is frozen out in cold traps 4a and 4b at about −80° C. The permeate and the vessel contents are analyzed about once per hour. After startup, the feed is heated by thermostat 5 from room temperature to 95° C. in the course of an hour and kept at that temperature (time t$_1$). The temperature difference between the feed temperature T$_1$ (PVin) and the retentate temperature T$_2$ (PV out) is then on average about 2.8° C. After 11 hours (time t$_2$) the end product amounts to 409 g comprising 96% by weight of 1-methoxy-2-propanol and 4% by weight of water. 309 g containing 98% by weight of water and 2% by weight of 1-methoxy-2-propanol have permeated through the membrane with the flow rate decreasing from about 4.6 kg/m$^2$h to 1.2 kg/m$^2$h.

EXAMPLE 2

Continuous dewatering of 1-methoxy-2-propanol by pervaporation

Figure 2:
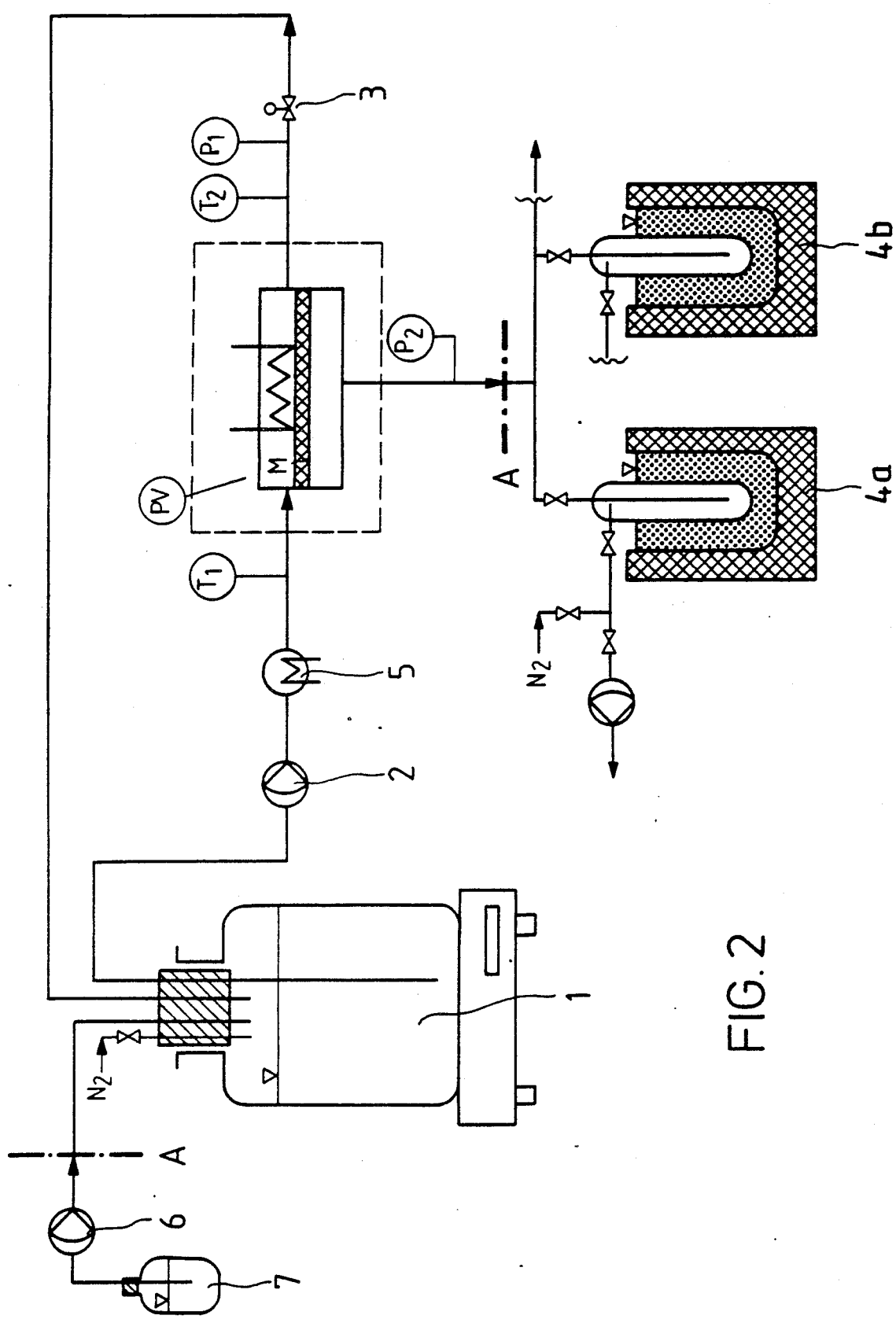
FIG. 2 shows a schematic depiction of a continuous process according to the present invention.

The continuous process is depicted in FIG. 2. It involves charging vessel 1 at room temperature with about 10 kg of a mixture of 86.8% by weight of 1-methoxy-2-propanol and 13.2% by weight of water. Pump 2 is recirculating the contents at about 5 kg/h. The membrane area M of the pervaporation cell measures 100 cm$^2$. A pressure of 2.5 bar is set at the pressure control valve 3. The permeate side is under an absolute pressure of 52 mbar. The permeate is either frozen out in cold traps 4a and 4b at about −80° C. or analyzed on-line by GC. After startup, the feed is heated by thermostat 5 from room temperature to 95° C. in the course of an hour and kept constant at that temperature. The temperature difference between feed temperature T$_1$ (PV in) and the retentate temperature T$_2$ (PV out) is then about 5.9° C. A metering pump 6 replenishes vessel 1 with mixture from reservoir 7 at approximately the same rate as permeate is produced in the pervaporation cell (section A—A). The permeate comprises 98.9% by weight of water and 1.1% by weight of 1-methoxy-2-propanol. The flow rate through the membrane is about 1.5 kg/m$^2$h. This steady state with a constant feed composition was kept in operation for about 21 hours.

The advantages obtained with the present invention reside in the fact that by working up the azeotrope it is possible to recover the solvent 1-methoxy-2-propanol and recycle it. In addition, there are no longer any costs for incinerating the azeotropic mixture.

We claim:

1. A process for separating water from a mixture of water and 1-methoxy-2-propanol, which process consists essentially of passing a mixture of water and 1-methoxy-2-propanol in gaseous or liquid form over a permeation membrane which has an input side and a permeate side and collecting the water from the permeate side.

2. The process of claim 1, wherein the permeation membrane is hydrophilic.

3. The process of claim 1, wherein the mixture is in gaseous form, the pressure on the input side of the membrane is 2.5 bar, and the pressure on the permeate side of the membrane is 25 mbar.

* * * * *